(12) United States Patent
Iwanaga

(10) Patent No.: US 7,470,025 B2
(45) Date of Patent: Dec. 30, 2008

(54) OPHTHALMIC APPARATUS

(75) Inventor: Tomoyuki Iwanaga, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 357 days.

(21) Appl. No.: 11/313,025

(22) Filed: Dec. 19, 2005

(65) Prior Publication Data

US 2006/0132711 A1 Jun. 22, 2006

(30) Foreign Application Priority Data

Dec. 21, 2004 (JP) ............................ 2004-368686

(51) Int. Cl.
*F16K 1/14* (2006.01)
*F16K 1/36* (2006.01)

(52) U.S. Cl. ...................... 351/211; 351/205
(58) Field of Classification Search ............ 351/211
See application file for complete search history.

(56) References Cited

U.S. PATENT DOCUMENTS

| | | | |
|---|---|---|---|
| 5,412,442 A | 5/1995 | Katsuragi et al. | |
| 6,494,577 B2 * | 12/2002 | Iwanaga | 351/208 |
| 7,029,120 B2 | 4/2006 | Kushida | |
| 7,210,781 B2 | 5/2007 | Kushida | |
| 2003/0076477 A1 * | 4/2003 | Matsumoto | 351/206 |
| 2003/0234908 A1 | 12/2003 | Kushida | |

FOREIGN PATENT DOCUMENTS

| | | |
|---|---|---|
| CN | 1301681 C | 2/2007 |
| JP | 8-206073 | 8/1996 |
| JP | 10-14878 | 1/1998 |
| JP | 10-118030 | 5/1998 |
| JP | 11-019045 | 1/1999 |

OTHER PUBLICATIONS

First Office Action for CN Application No. 2005101338105, dated Dec. 28, 2007.
Notification of the First Office Action for CN Application No. 2005101338105, dated Dec. 28, 2007.
English translation of text portion of First Office Action for CN Application No. 2005101338105, dated Dec. 28, 2007.
CN Application No. 1468582A, dated Jan. 21, 2004.

* cited by examiner

Primary Examiner—Jordan M. Schwartz
Assistant Examiner—James C Jones
(74) Attorney, Agent, or Firm—Morgan & Finnegan LLP

(57) ABSTRACT

There is disclosed an ophthalmic apparatus including a detection unit which detects a vision fixation state of an eye to be examined, a projection unit which projects a fixation mark onto a fundus of the eye, and a fixation mark control unit which controls the projection unit. The projection unit includes a changing unit which changes a fixation mark to be projected onto the fundus, and when a vision fixation state detected by the detection unit does not satisfy a predetermined criterion, the fixation mark control unit controls the changing unit to change a fixation mark to be projected onto the fundus.

20 Claims, 8 Drawing Sheets

OPHTHALMIC APPARATUS

FIELD OF THE INVENTION

The present invention relates to an ophthalmic apparatus which, for example, examines an eye to be examined or photographs the eye or observes it.

BACKGROUND OF THE INVENTION

In an ophthalmic apparatus designed to obtain information unique to an eye to be examined by projecting a light beam onto the eye and receiving the reflected light, a fixation mark for stabilizing a vision fixation state by fixing the eye is provided.

There has recently been known an ophthalmic apparatus which includes a detection means for detecting a light beam projected onto the cornea or the like of an eye to be examined, and a driving means for moving an eye examination unit in the up and down direction, the left and right direction, and the back and forth direction, or any thereof, and aligns the eye with an apparatus optical system by controlling the driving means on the basis of the detected eye position.

In such an ophthalmic apparatus, an examiner roughly aligns an eye to be examined with an eye examination unit by operating an operation means such as a console or a trackball so as to depict an image of the eye on a monitor to some extent, and presses a measurement switch upon completion of the alignment. When the measurement switch is pressed, the relative position between the eye and the eye examination unit is detected, and the driving means is controlled to make the eye examination unit coincide with the position of the eye. When the misalignment between the eye and the eye examination unit reaches a value within a predetermined allowable amount, ophthalmic examination such as measurement or photography is started.

The ophthalmic apparatus disclosed in Japanese Patent Laid-Open No. 10-14878 includes a vision fixation state determination means for determining the quality of the vision fixation state of an eye to be examined on the basis of detection results obtained by a pupil detection means and an alignment index projection/detection optical system. This apparatus detects the vision fixation state of the eye and starts measurement when determining that the vision fixation state of the eye is proper.

The fundus photographing apparatus disclosed in Japanese Patent Laid-Open No. 10-118030 has a plurality of fixation marks having different sizes which are presented to eyes to be examined, and can present a subject to be examined who has a visual disorder such as cataract or amblyopia with a large fixation mark which is easy to visually recognize.

According to the ophthalmic apparatus in Japanese Patent Laid-Open No. 10-14878, if a subject to be examined is, for example, a person who has a visual disorder such as cataract or amblyopia or an infant, it is difficult to make the subject determine where the fixation mark is located. In examining such a subject, therefore, the vision fixation state determination means for determining the quality of the vision fixation state of an eye to be examined determines a fixation failure on the basis of detection results obtained by the pupil detection means and the alignment index projection/detection optical system. In this case, a measurement permission is not issued, and the examination time prolongs. As a result, the vision fixation state of the eye becomes more unstable, and the measurement lasts forever.

The fundus photographing apparatus in Japanese Patent Laid-Open No. 10-118030 presents a subject to be examined who has a visual disorder such as cataract or amblyopia with a large fixation mark which is easy to visually recognize. Assume that the initial position of the optical axis direction of a fixation mark presented by the ophthalmic apparatus greatly differs from the line of sight of an eye to be examined. In this case, even if a large fixation mark is presented to the eye, the subject cannot recognize where the fixation mark is located, and it may be difficult to stabilize the line of sight.

If, therefore, a person who has poor eyesight, an infant, or the like is a subject to be examined, such a conventional ophthalmic apparatus cannot make the subject recognize where a fixation mark is located, and hence it is difficult to stabilize a vision fixation state. As a consequence, the accuracy of automatic alignment deteriorates, and the reliability of examination deteriorates. In addition, the examination time prolongs. In some cases, alignment cannot be completed, and examination cannot be performed.

SUMMARY OF THE INVENTION

The present invention has been made on the basis of the recognition of the above problems, and has as its object to execute examination of an eye to be examined and photography or observation thereof, and the like more stably and smoothly by, for example, improving the stability of a vision fixation state.

According to a first aspect of the present invention, there is provided an ophthalmic apparatus comprising a detection unit which detects a vision fixation state of an eye to be examined, a projection unit which projects a fixation mark onto a fundus of the eye, and a fixation mark control unit which controls the projection unit, wherein the projection unit includes a changing unit which changes a fixation mark to be projected onto the fundus, and the fixation mark control unit controls the changing unit to change a fixation mark to be projected onto the fundus when a vision fixation state detected by the detection unit does not satisfy a predetermined criterion.

According to a second aspect of the present invention, there is provided an ophthalmic apparatus comprising an observation unit which observes an anterior ocular segment of an eye to be examined by illuminating the anterior ocular segment and sensing an image thereof, an alignment index detection unit which detects a cornea reflected index image of an alignment index for position detection upon projecting the alignment index onto the cornea of the eye, a line-of-sight detection unit which detects a line of sight of the eye based on outputs from the observation unit and the alignment index detection unit, a determination unit which determines whether a vision fixation state of the eye detected by the line-of-sight detection unit satisfies a predetermined condition, a fixation mark projection unit which projects a fixation mark onto a fundus of the eye, a fixation mark presentation changing unit which changes a presentation method for the fixation mark projected by the fixation mark projection unit, and an arithmetic processing unit, wherein when the determination unit determines that a vision fixation state detected by the line-of-sight detection unit does not satisfy the predetermined condition, the arithmetic processing unit controls the fixation mark presentation changing unit to change the presentation method for the fixation mark.

The changing of the fixation mark projected onto the fundus according to the first aspect or the changing of the presentation method for the fixation mark according to the second aspect can include, for example, the changing of the brightness and size of a fixation mark to be projected onto the fundus and changing operation of emphasizing the existence of a fixation mark by applying stimulus to a subject to be examined, e.g., blinking of light.

In an ophthalmic apparatus according to a preferred embodiment of the present invention, an alignment index is projected onto the cornea of an eye to be examined, and the position of the index image is detected. If it is determined that the position of the index image with respect to the optical axis exceeds a predetermined condition such as a time, a range, a moving speed, or the misalignment between the pupil center and the position of the index image, a fixation mark to be projected onto the fundus or the method of presenting a fixation mark to the eye is changed. This makes it possible to emphasize the existence of the fixation mark with respect to the eye and make the subject pay attention, thereby urging the subject to stabilize his/her vision fixation. As a consequence, this can reduce the burden on the subject and shorten the examination time.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

The present invention will be described in detail with reference to the embodiments shown in the accompanying drawings.

First Embodiment

Figure 1:
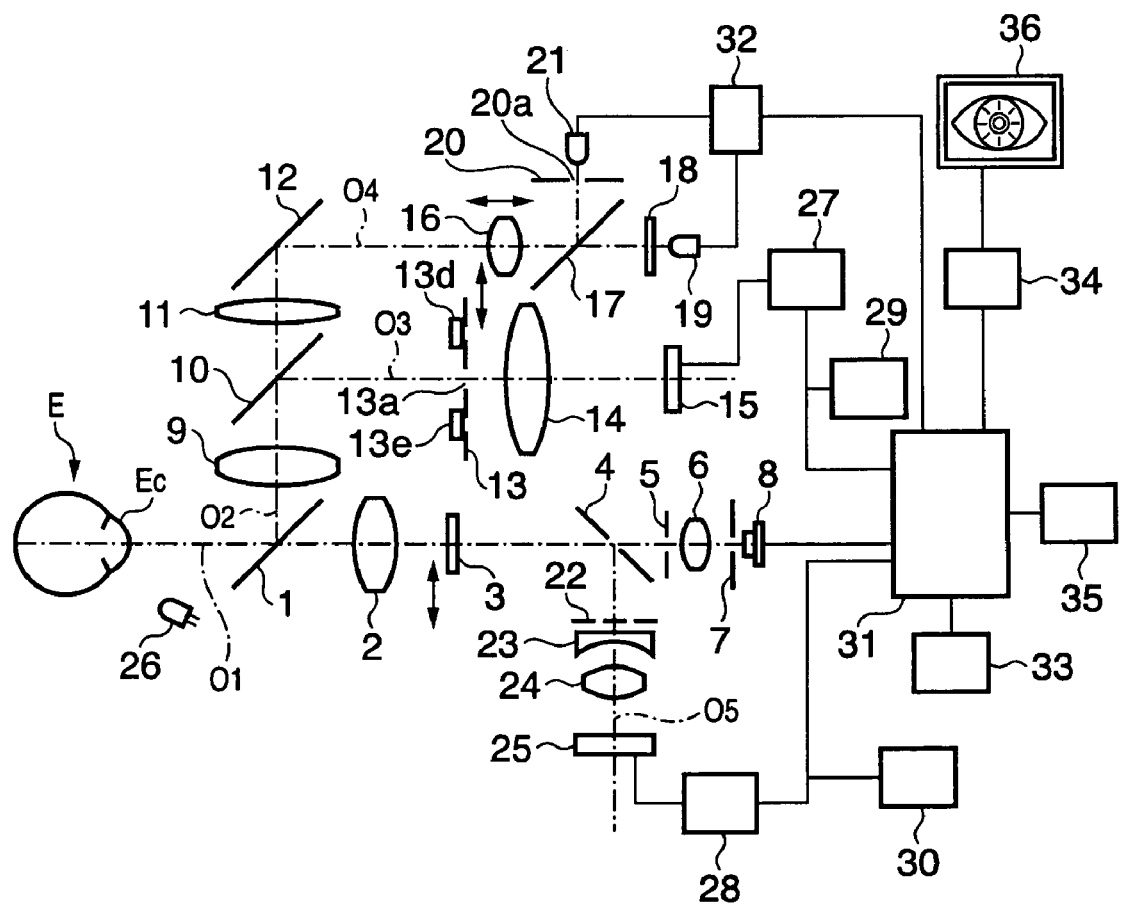
FIG. 1 is a view showing the arrangement of the first embodiment of the present invention.

FIG. 1 is a view showing the arrangement of an ocular refractive power measuring apparatus (ophthalmic apparatus) according to the first embodiment of the present invention. On an optical axis O1 facing an eye E to be examined, there are sequentially arranged a dichroic mirror 1, an objective lens 2 for the measurement of an ocular refractive power, a diffuser 3 which is detachable with respect to the optical axis O1, a perforated mirror 4, a projection stop 5, a projection lens 6, an index plate 7 having a pinhole, and a light source 8 for the measurement of an ocular refractive power. These components constitute a measurement light projection system for the measurement of an ocular refractive power.

On an optical axis O2 in the reflecting direction of the dichroic mirror 1, there are arranged an objective lens 9 for the observation of the anterior ocular segment, a dichroic mirror 10 having the property of transmitting visible light and reflecting near-infrared light, a lens 11, and a mirror 12. On an optical axis O3 in the reflecting direction of the dichroic mirror 10, a stop plate 13 like the one shown in FIG. 12 which is detachably placed on the optical axis O3, an imaging lens 14, and an image sensing device 15 such as a CCD camera are arranged. The image sensing device 15 is placed at a position almost conjugate to a position near the anterior ocular segment of the eye E. An anterior ocular segment observation system is comprised of the objective lens 9 for the observation of the anterior ocular segment, the dichroic mirror 10, the stop plate 13, the imaging lens 14, and the image sensing device 15.

Figure 2:
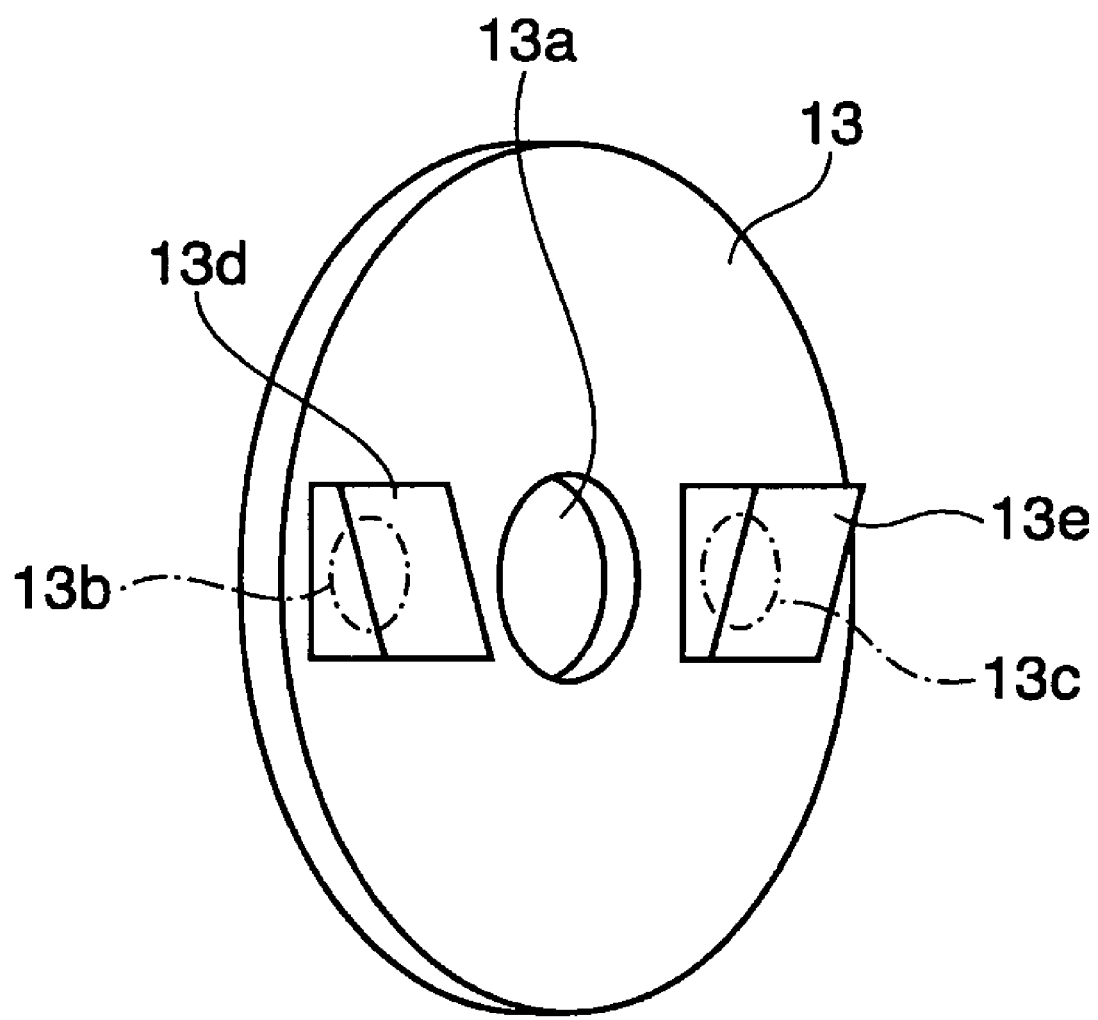
FIG. 2 is a perspective view of a stop plate.

As shown in FIG. 2, the stop plate 13 has an aperture 13a on the optical axis O3, and also has two symmetrical apertures 13b and 13c located on both sides of the optical axis. The stop plate 13 has polarizing prisms 13d and 13e on the portions in which the apertures 13b and 13c are formed. Note that the polarizing prisms 13d and 13e have the spectral characteristics of transmitting light with the first wavelength from the light source 8 for ocular refractive power measurement but not transmitting light with the second wavelength from a light source 26 for anterior ocular segment illumination. The polarizing prism 13d deflects a light beam to above the drawing surface. The polarizing prism 13e deflects a light beam to below the drawing surface.

Figure 3:
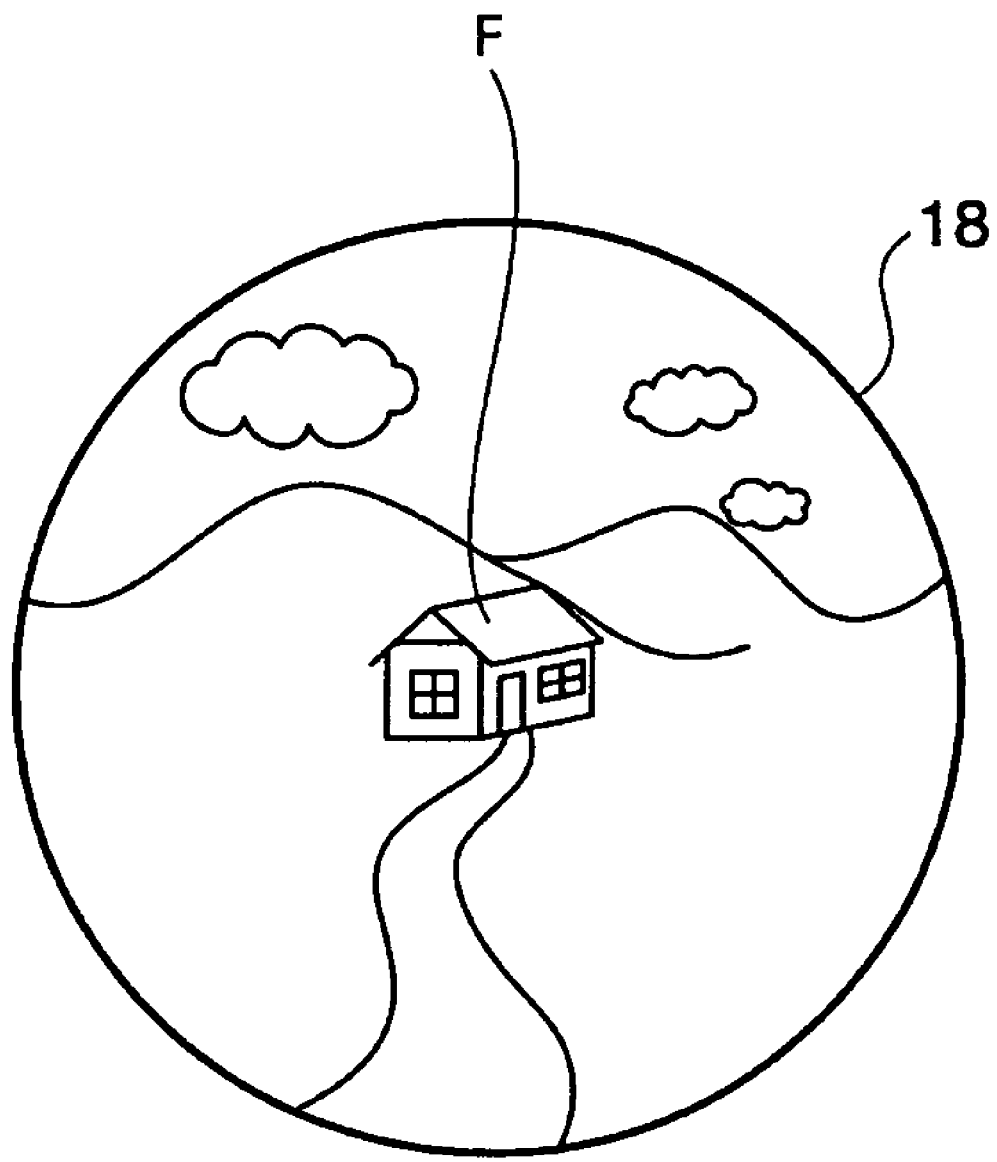
FIG. 3 is a view for explaining a fixation mark having a fixation target.
Figure 4:
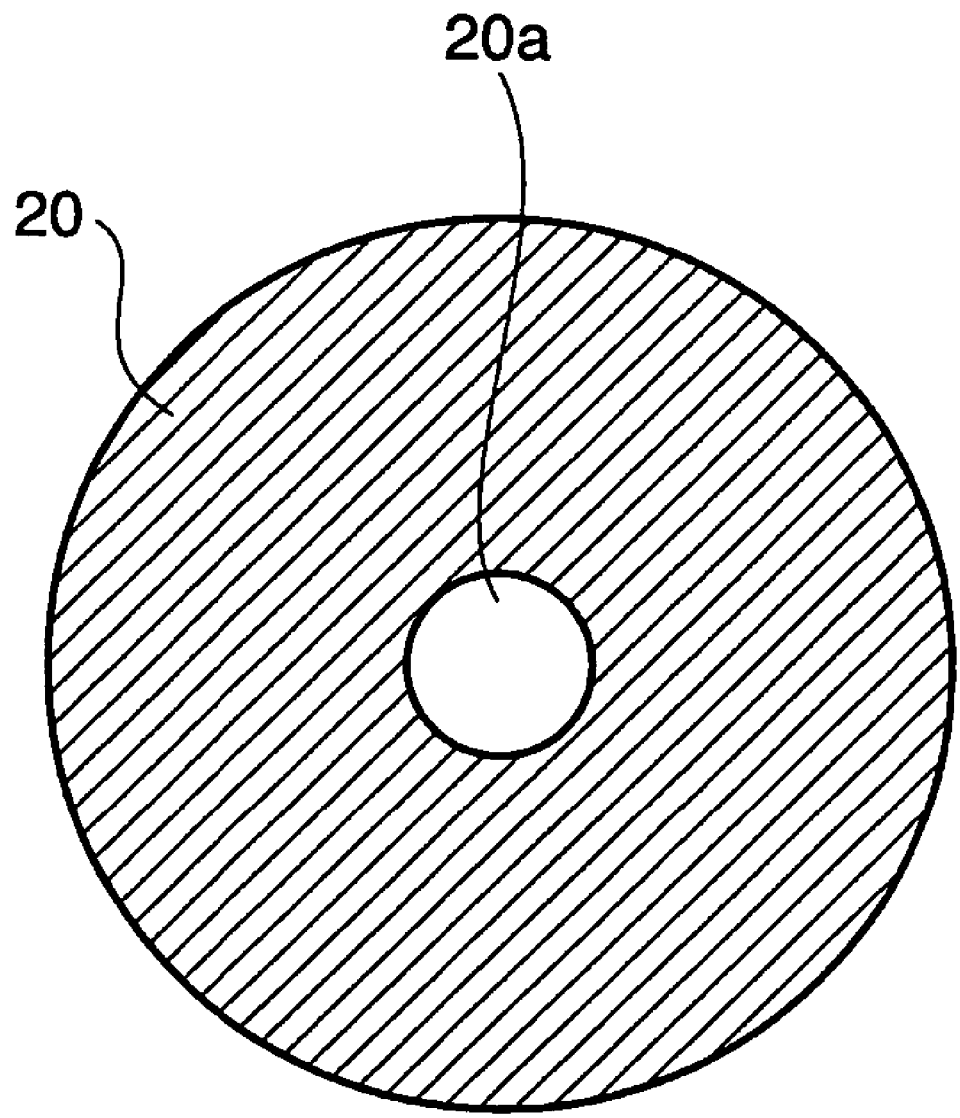
FIG. 4 is a front view of a fixation mark plate.

On an optical axis O4 in the reflecting direction of the mirror 12, there are arranged a fixation mark projection lens 16 which can move in the direction of the optical axis O4, a beam splitter 17, a fixation mark 18 having a fixation target F like the one shown in FIG. 3, and a light source 19 for fixation mark illumination such as a white LED which emits light having a white wavelength. A fixation mark plate 20 having a pinhole 20a like the one shown in FIG. 4 and a light source 21 for fixation mark illumination such as an LED which emits light having a green wavelength are provided in the reflecting direction of the beam splitter 17.

A fixation mark projection system which projects a fixation mark for the fixation of the eye E is comprised of the lens 9 for observation of anterior ocular segment, dichroic mirror 10, lens 11, mirror 12, fixation mark projection lens 16, beam splitter 17, fixation mark 18, light source 19 for fixation mark illumination, fixation mark plate 20, and light source 21 for fixation mark illumination. The first fixation mark is formed by the fixation mark 18 and the light source 19 for fixation mark illumination. The second fixation mark is formed by the fixation mark plate 20 and the light source 21 for fixation mark illumination.

A 6-aperture stop 22 having six apertures, a 6-piece prism 23, a relay lens 24, and an image sensing device 25 such as a CCD camera are arranged on an optical axis O5 in the reflecting direction of the perforated mirror 4, thereby forming a light-receiving system for the measurement of an ocular refractive power.

The light source 26 for anterior ocular segment illumination such as an LED which emits near-infrared light having a wavelength shorter than light emitted from the light source 8 for ocular refractive power measurement, which irradiates the anterior ocular segment of the eye E, by several 10 nm is placed between the eye E and the dichroic mirror 1 in front of the eye.

The dichroic mirror 1 has the property of transmitting most of light with the first wavelength emitted from the light source 8 for ocular refractive power measurement while reflecting part of the light, and reflecting light with the second wavelength emitted from the light source 26 for anterior ocular segment illumination. The diffuser 3 is placed to diffuse a light beam emitted from the light source 8 for ocular refractive power measurement and has high forward scattering intensity, so that most of a scattered light beam is focused by the objective lens 2 for ocular refractive power measurement.

Outputs from the image sensing devices 15 and 25 are respectively output to A/D converters 27 and 28. Outputs from the A/D converters 27 and 28 are then provided for image memories 29 and 30, and are also provided for an arithmetic processing unit (control unit) 31 which controls the overall apparatus. An output of the arithmetic processing unit 31 is connected to the light sources 19 and 21 for fixation mark illumination through a fixation mark light source control unit 32. In addition, the light source 8 for ocular refractive power measurement, an operation unit 33 having a measurement start switch, a switch for operating the driving unit, and the like, a D/A converter 34, and a driving unit 35 such as a motor are connected to the arithmetic processing unit 31. In addition, an output from the D/A converter 34 is provided for a monitor 36 which depicts an image. Note that a printer which prints information may be connected to the arithmetic processing unit 31.

The eye examination unit is comprised of the above anterior ocular segment observation system, fixation mark projection system, projection system for ocular refractive power measurement light, ocular refractive power measurement light-receiving system, and the like. The eye examination unit is mounted on a base which can move in the three axis directions. The base can be motor-driven by the driving unit 35.

Figure 5A:
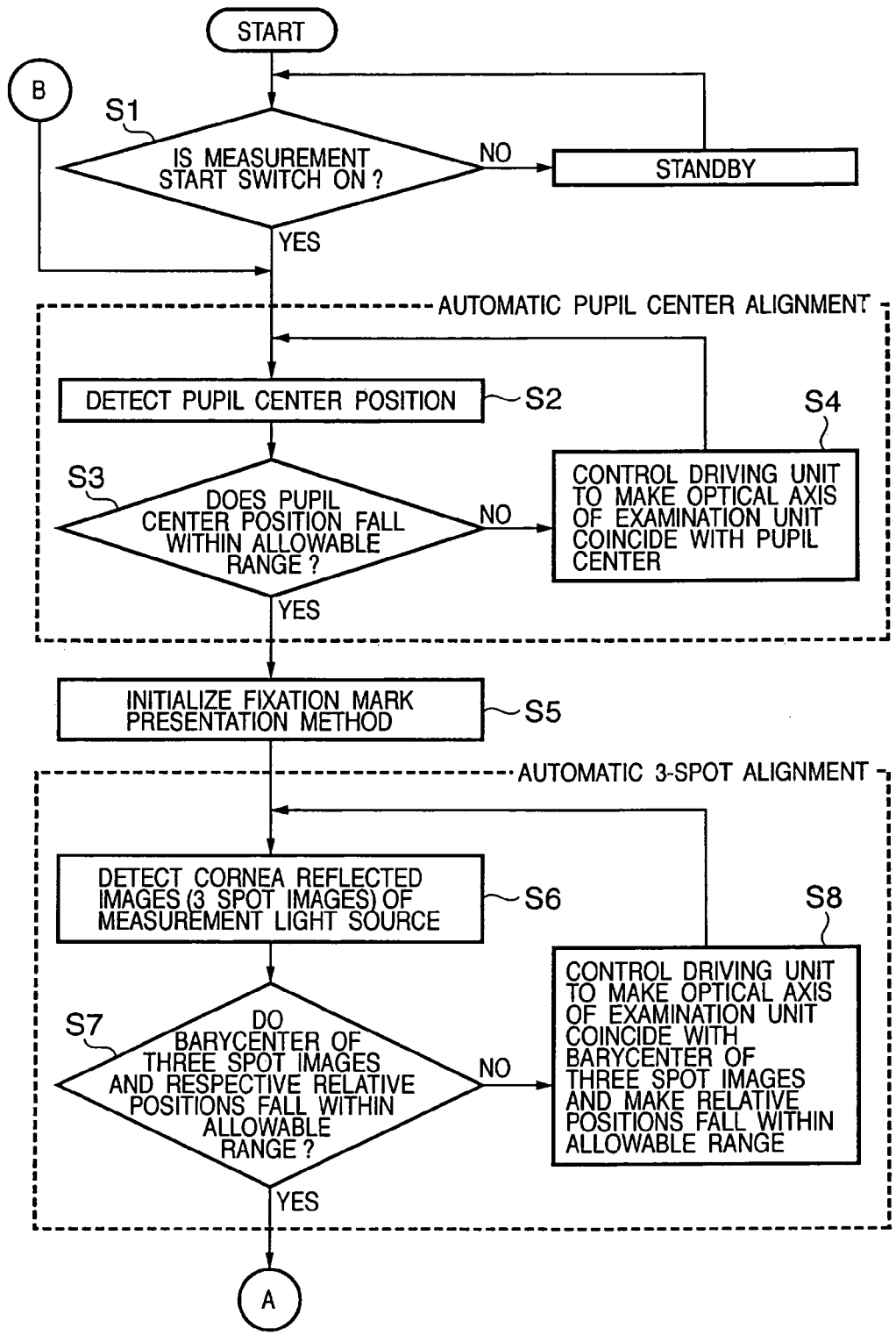
FIGS. 5A and 5B are flowcharts showing operation.
Figure 5B:
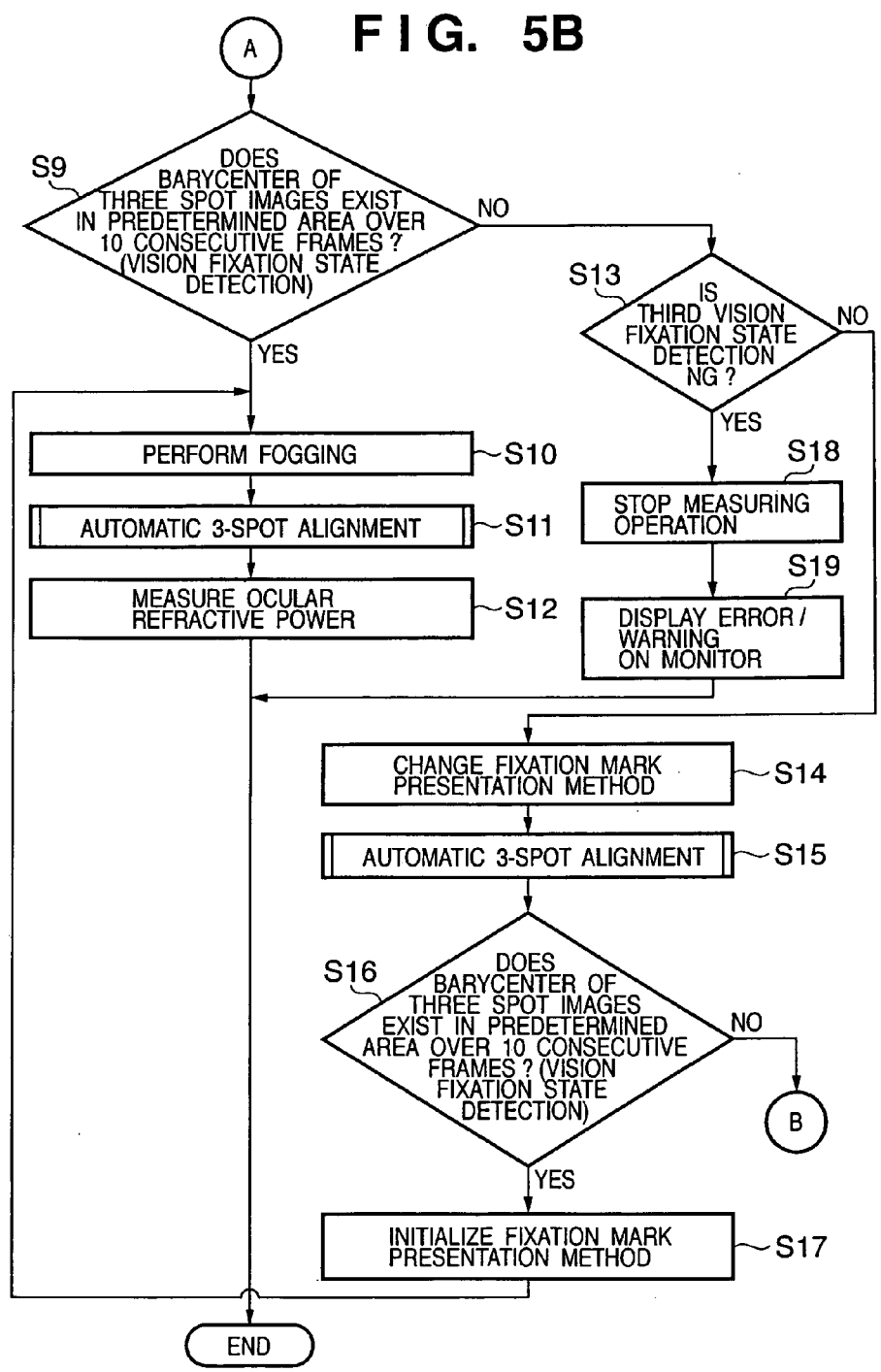

FIGS. 5A and 5B are flowcharts for explaining the operation of the ocular refractive power measuring apparatus shown in FIG. 1. At the start, the examiner performs rough alignment by operating the trackball of the operation unit 33 so as to depict a right eye Er of a subject to be examined on the monitor 36. At this time, a light beam from the fixation mark 18 illuminated by the light source 19 for fixation mark illumination is transmitted through the beam splitter 17 and is transmitted through the dichroic mirror 10 via the fixation mark projection lens 16, mirror 12, and lens 11, thereby presenting the fixation mark 18 to the eye E through the lens 9 for observation of anterior ocular segment and the dichroic mirror 1. As a result, an initial state is set.

When the measurement start switch of the operation unit 33 is pressed in step S1 to execute automatic pupil center alignment, the arithmetic processing unit 31 starts measuring operation. In step S2, the arithmetic processing unit 31 causes the light source 26 for anterior ocular segment illumination to illuminate the eye E. The reflected scattered light from around the anterior ocular segment of the eye E illuminated by the light source 26 for anterior ocular segment illumination is reflected by the dichroic mirror 1, converted into almost parallel light by the lens 9 for observation of anterior ocular segment, and reflected by the dichroic mirror 10. This light then passes through the aperture 13a of the stop plate 13 and forms an image on the image sensing device 15 through the imaging lens 14.

An output signal from the image sensing device 15 is converted into a digital signal by the A/D converter 27 and is depicted as an anterior ocular segment image E' on the monitor 36 through the arithmetic processing unit 31 and the D/A converter 34. At the same time, the anterior ocular segment image data of the eye E converted into the digital signal is stored in the image memory 29. The arithmetic processing unit 31 extracts the pupil of the right eye Er from the stored anterior ocular segment image data and detects the pupil center position.

According to this pupil center position detection method, if, for example, the anterior ocular segment to be examined is sufficiently illuminated, the brightness of the anterior ocular segment image is lowest at the pupil and gradually increases in the order of the iris and the sclera. Therefore, performing binarization processing with an appropriate threshold makes it possible to obtain the boundary of the pupil and calculate the pupil center position.

When the pupil center position is detected, in step S3, the arithmetic processing unit 31 calculates the amount of misalignment between the optical axis O1 of the eye examination unit and the pupil center position within a plane perpendicular to the optical axis, and determines whether the amount of misalignment between the pupil center position and the optical axis O1 falls within a predetermined allowable range. If the amount of misalignment between the pupil center position and the apparatus measurement optical axis O1 falls outside the allowable range, the flow advances to step S4. In step S4, the arithmetic processing unit 31 controls the driving unit 35 such as a motor to make the optical axis of the eye examination unit coincide with the pupil center position, and returns the flow to step S2. In step S2, the pupil center position is detected again in this manner. In step S3, it is determined whether the amount of misalignment between the pupil center position and the apparatus measurement optical axis falls within the allowable range.

If automatic pupil center alignment is performed in steps S2 to S4 and it is determined that the amount of misalignment between the pupil center position and the apparatus measurement optical axis O1 falls within the allowable range ("Y" in step S3), the flow advances to step S5, in which the arithmetic processing unit 31 sets the above fixation mark presentation method in the initial state if the fixation mark presentation method is not in the initial state.

Subsequently, in order to perform automatic 3-spot alignment, the arithmetic processing unit 31 turns on the light source 8 for ocular refractive power measurement and detects a reflected image from the cornea in step S6. In this case, the light beam emitted from the light source 8 for ocular refractive power measurement illuminates the index plate 7, and a light beam transmitted through the pinhole of the index plate 7 forms a pinhole image of the index plate 7 on the diffuser 3 inserted in the rear-side focal plane of the objective lens 2 for ocular refractive power measurement through the projection stop 5. The light beam diffused by the diffuser 3 is converted into almost parallel light by the objective lens 2 for ocular refractive power measurement. Most of this light is transmitted through the dichroic mirror 1 and reaches the eye E.

A light beam from a two-dimensional light source on the diffuser 3 which has reached the eye E is reflected by a cornea Ec of the eye E, and forms a cornea reflected index image of the reflected light beam at the position of the middle point between the cornea curvature center and the cornea vertex. Part of the light beam is reflected by the dichroic mirror 1 and is converted into almost parallel light by the lens 9 for observation of anterior ocular segment. In addition, the light beam is deflected in the direction of the optical axis O3 by the dichroic mirror 10, and is split into three light beams by the apertures 13a, 13b, and 13c of the stop plate 13 having the polarizing prisms 13d and 13e. These light beams reach the image sensing device 15 through the imaging lens 14, and their images are sensed together with an anterior ocular segment image of the eye. An output from the image sensing device 15 is digitized by the A/D converter 27 and stored in the image memory 29. The arithmetic processing unit 31 detects three spot images from the image data stored in the image memory 29.

In step S7, the arithmetic processing unit 31 detects the relative position between the eye examination unit and the eye E from the barycentric position of the three detected spot images and the respective relative positions, and determines on the basis of the detection result whether the eye examination unit is in a predetermined positional relationship with the eye E. If the positional relationship between the eye examination unit and the eye E falls outside an allowable range, the flow advances to step S8, in which the arithmetic processing unit 31 controls the driving unit 35 to set the optical axis O1 of the eye examination unit and the eye E in a predetermined positional relationship. The flow then returns to step S6. After three spot images are detected in step S6 again in this manner, it is determined in step S7 whether the eye examination unit and the eye E are in the predetermined positional relationship.

If automatic 3-spot alignment is performed in this manner in steps S6 to S8 and it is determined that the positional relationship between the eye examination unit and the eye E falls within the allowable range, the flow advances to step S9.

In step S9, the arithmetic processing unit 31 detects the vision fixation state of the eye E and determines whether the vision fixation state is stable. In the first embodiment, the image sensing device 15 used for the detection of three spot images is, for example, a CCD camera. This CCD camera generally senses images at a rate of 30 frames per sec. The arithmetic processing unit 31 detects the pupil center position and the barycentric position of three spot images which are cornea reflected images from the stop plate 13, and obtains the relative positional variation amount between the pupil center position and the barycentric position of the three spots, thereby detecting a line of sight. If, for example, the detected line of sight exhibits allowable variations in ocular refractive power measurement during 10 consecutive frames, the arithmetic processing unit 31 determines that the vision fixation state is stable.

The detection of a vision fixation state is not limited to this. For example, if the barycenter of three spot images exists within a predetermined area at a predetermined ratio or more with respect to a plurality of frames, it may be determined that the vision fixation state is stable. Alternatively, the barycentric position of the middle spot image of three detected spot images may be obtained for each frame, and it may be determined that the vision fixation state is stable, if the moving speed and moving amount of the middle spot image fall within preset conditions.

When the alignment between the eye E and the eye examination unit is complete in this manner, and it is determined that the vision fixation state of the eye E is stable, the flow advances to step S10, in which the arithmetic processing unit 31 promotes fogging for the eye E. First of all, the arithmetic processing unit 31 retracts the inserted diffuser 3 out of the optical path, and turns on the light source 8 for ocular refractive power measurement to illuminate the pinhole of the index plate 7. With this operation, the pinhole image of the index plate 7 is transmitted through the projection lens 6, the projection stop 5, the hole of the perforated mirror 4, the objective lens 2 for ocular refractive power measurement, and the dichroic mirror 1, and is projected onto the fundus of the eye E.

The light beam reflected and scattered by the pinhole image of the index plate 7, as the secondary light source, which is projected onto the fundus of the eye E exits from the pupil and cornea of the eye E, and is transmitted through the dichroic mirror 1. This light beam is focused by the objective lens 2 for ocular refractive power measurement and is reflected by a peripheral portion of the perforated mirror 4. The light beam is split into six light beams by the respective apertures of the 6-aperture stop 22. The six light beams strike the image sensing device 25 through the 6-piece prism 23 and the relay lens 24, and their images are sensed by the image sensing device 25 as six images. Thereafter, the arithmetic processing unit 31 turns off the light source 8 for ocular refractive power measurement.

An output from the image sensing device 25 is digitized by the A/D converter 28 and recorded on the image memory 30. The arithmetic processing unit 31 then calculates a refracting power D1 before fogging of the eye E. The arithmetic processing unit 31 moves the fixation mark projection lens 16, which is movable in the direction of the optical axis O4, to set the fixation mark 18 at a position spaced away from a conjugate position on the optical axis O4 by a dioptre of +0.5 with respect to the refracting power D1 obtained before fogging.

The arithmetic processing unit 31 turns on the light source 8 for ocular refractive power measurement again to project a light beam onto the fundus of the eye E, causes the image sensing device 25 to sense the image of reflected scattered light from the fundus, and calculates a refracting power D2. The arithmetic processing unit 31 sets the fixation mark 18 at a position spaced apart from a conjugate position on the optical axis O4 by a dioptre of +0.5 with respect to the refracting power D2 obtained before fogging. The arithmetic processing unit 31 repeats the above operation in this manner. Such operation is repeated until the refracting power of the eye E cannot follow-up the optical position of the fixation mark 18 on the optical axis O4. This makes it possible to relax the accommodation of the eye E and set the eye in a fogging (farsightedness) state.

When the eye E is set in the fogging state, the arithmetic processing unit 31 performs automatic 3-spot alignment again in step S11. When this automatic 3-spot alignment is complete, the flow advances to step S12 to perform ocular refractive power measurement of the eye E by a known method a predetermined number of times. This processing is then terminated. In this case, after automatic 3-spot alignment, vision fixation state detection may be performed again.

Assume that in step S9, in examining a person who has amblyopia, an infant, or the like, the subject cannot recognize where a fixation mark is located, and hence a vision fixation state is not stable. In this case, the vision fixation state of the eye E is detected, and it is determined that the vision fixation state is not stable. The flow then advances to step S13. It is determined in step S13 whether the number of times a vision fixation state failure is determined has reached a predetermined number of times (e.g., three times). If a vision fixation state failure is detected for the first time or the second time, the flow advances to step S14, in which the arithmetic processing unit 31 changes the fixation mark presentation method and emphasizes the existence of the fixation mark with respect the eye E.

In the first embodiment, the light source 19 for fixation mark illumination which emits light with a white wavelength is turned off (the projection of the first fixation mark is stopped), and the light source 21 for fixation mark illumination which emits light with a green wavelength is turned on and off (the second fixation mark is intermittently projected). Light from the light source 21 for fixation mark illumination passes through the pinhole 20a of the fixation mark plate 20, and is reflected by the beam splitter 17. This light is then transmitted through the dichroic mirror 10 via the fixation mark projection lens 16, mirror 12, and lens 11, and is projected as the second fixation mark onto the eye E through the objective lens 9 and the dichroic mirror 1.

A subject to be examined who has amblyopia can recognize the existence of the fixation mark plate 20 because its index light beam blinks. A subject to be examined like an infant unconsciously sees the direction of the fixation mark plate 20 because an index light beam from the fixation mark plate 20 blinks. As a consequence, the vision fixation state of the infant is stabilized.

Subsequently, in step S15, the arithmetic processing unit 31 performs automatic 3-spot alignment again after the fixation mark presentation method is changed. When this automatic alignment is complete, the arithmetic processing unit 31 advances to step S16 to detect the vision fixation state of the eye E and determine whether the vision fixation state is stable, as in step S9. If it is determined that the vision fixation state of the eye E is stable, the flow advances to step S17 to initialize the fixation mark presentation method as in step S5.

This initial state of the fixation mark presentation method is the state in which a light beam from the fixation mark 18 illuminated by the light source 19 for fixation mark illumination is presented to the eye E through the fixation mark projection system, as described above. After the fixation mark presentation method is initialized in this manner in step S17, the flow advances to steps S10, S11, and S12 to perform ocular refractive power measurement.

At this time, the ocular refractive power measurement result is displayed on the monitor 36 and is printed by a printer (not shown), together with a symbol representing the hierarchical level of the vision fixation state at the time of measurement, thereby providing a reference for the reliability of the measurement result. Alternatively, variations in vision fixation state may be displayed or printed as a graph with the amplitudes representing variations in the relative position between an obtained pupil center position and the barycentric position of the three spots and the abscissa representing the time axis.

In addition, the vision fixation state of an eye to be examined can be obtained more accurately by subtracting the amount of misalignment between the barycenter of three spots and an examination optical axis from a variation in the relative position between the pupil center position and the barycentric position of the three spots.

If it is determined in step S16 that the vision fixation state is not stable, the flow returns to step S2 to detect a pupil center position again.

If it is determined by the third vision fixation state determination in step S13 that the vision fixation state is faulty, the flow advances to step S18, in which the arithmetic processing unit 31 stops the measuring operation. In step S19, the arithmetic processing unit 31 then terminates the measuring operation after displaying, on the monitor 36, an error message or warning indicating that the measuring operation is stopped because the vision fixation state is unstable.

Note that in vision fixation state detection in step S9, a change in the relative position between the pupil center position and the positions of three spot images as cornea reflected images may be detected, and it may be determined that the vision fixation state is stable, if the change in relative position falls within a predetermined range within a predetermined period of time.

As described above, in the first embodiment, a position detection index is projected onto the cornea Ec of the eye E, and the position of an index image is detected. If the position of the index image with respect to the apparatus optical axis exceeds a predetermined condition such as a time, a range, a moving speed, or the misalignment between the pupil center and an index image, the fixation mark projected onto the fundus or the fixation mark presentation method (a stimulus to be applied to an eye to be examined) is changed by changing the brightness, color, shape, or the like of the fixation mark. This makes it possible to emphasize the existence of a fixation mark with respect to an eye to be examined and make the subject pay attention, thereby urging the subject to stabilize his/her vision fixation. As a consequence, this can reduce the burden on the subject and shorten the examination time.

Second Embodiment

Figure 6:
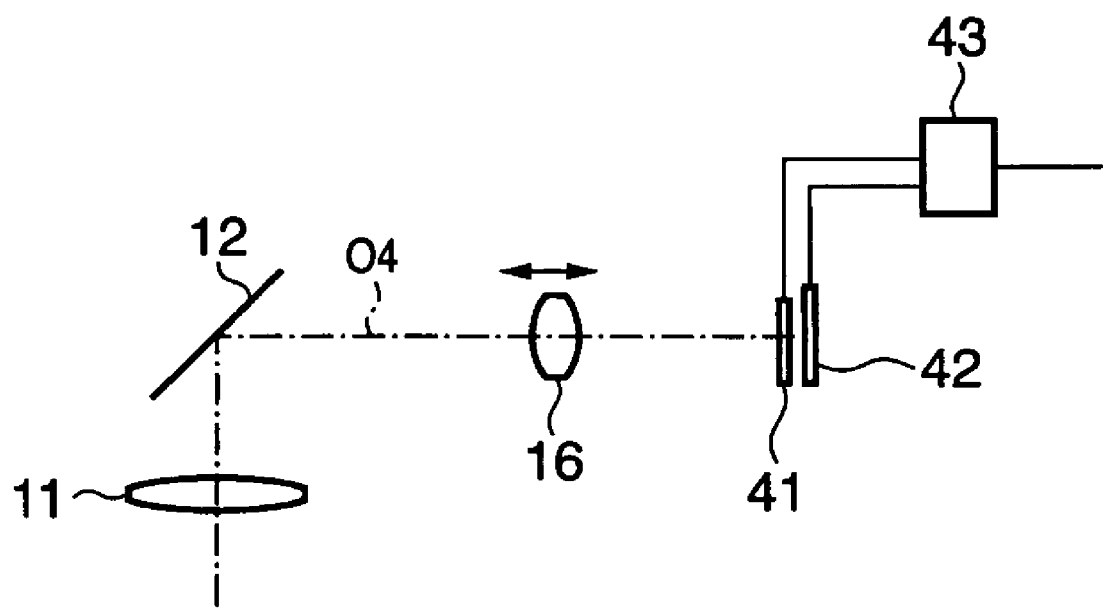
FIG. 6 is a view showing the arrangement of a fixation mark projection system according to the second embodiment of the present invention.

FIG. 6 is a view showing the arrangement of a fixation mark projection system according to the second embodiment of the present invention. The same reference numerals as in the first embodiment denote the same parts in the second embodiment. In addition, since an anterior ocular segment observation system, a projection system for ocular refractive power measurement light, an ocular refractive power measurement light-receiving system, an arithmetic processing unit 31, and the like, other than the fixation mark projection system, have the same arrangements as those in the first embodiment, an illustration thereof will be omitted.

Figure 7A:
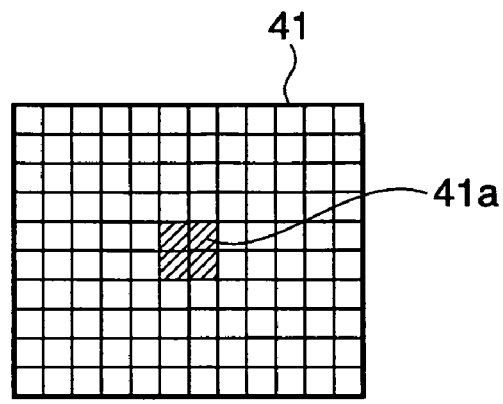
FIGS. 7A to 7C are views for explaining fixation target patterns.
Figure 7B:
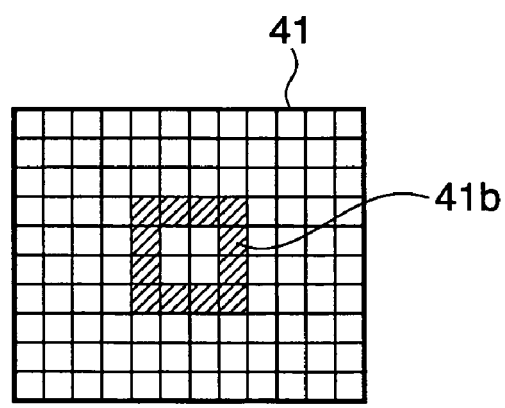
Figure 7C:
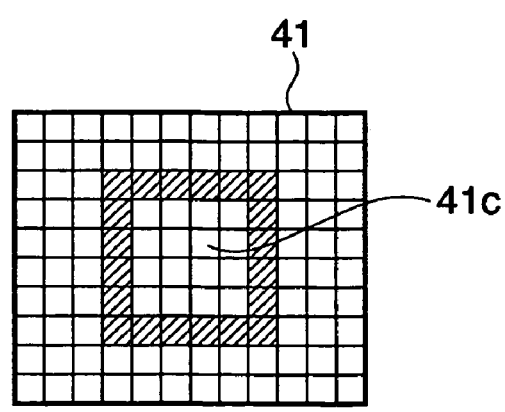

In the fixation mark projection system of the second embodiment, a fixation mark 41 comprising, for example, liquid crystal panels shown in FIGS. 7A to 7C and a light source 42 for fixation mark illumination for a liquid crystal backlight for illuminating the fixation mark 41 are arranged on an optical axis O4. A fixation mark control unit 43 which controls graphic patterns to be displayed and brightness is connected to the fixation mark 41 and light source 42 for fixation mark illumination. The fixation mark control unit 43 is connected to the arithmetic processing unit 31 which performs control on the apparatus, arithmetic processing, and the like.

A light beam from the fixation mark 41 illuminated by the light source 42 for fixation mark illumination is transmitted through a dichroic mirror 10 via a fixation mark projection lens 16, mirror 12, and lens 11, and reaches an eye E to be examined through an lens 9 for observation of anterior ocular segment and a dichroic mirror 1. At this time, the fixation mark 41 has a small light-impermeable area like a pattern 41a in FIG. 7A in the center of the optical axis. The eye E recognizes the pattern 41a as a fixation mark.

In the second embodiment, a state wherein the pattern 41a is presented as a fixation mark is the initial state of a fixation mark presentation method. The flow of operation in the second embodiment is almost the same as that in the first embodiment, and conforms to the flowchart shown in FIGS. 5A and 5B. However, the changing of the fixation mark presentation method in step S14 is performed as follows in the second embodiment.

If it is determined in step S9 that the vision fixation state of the eye E is faulty, the arithmetic processing unit 31 sequentially changes the fixation mark to be displayed on the fixation mark 41 from the pattern 41a to patterns 41b and 41c, which are shown in FIGS. 7A, 7B, and 7C, respectively, thereby changing the shape and size of the fixation mark. In this case, the luminance of the light source 42 for fixation mark illumination may be changed in synchronism with the change of the fixation marks so as to allow the eye E to recognize the fixation mark more easily.

As many apparently widely different embodiments of the present invention can be made without departing from the spirit and scope thereof, it is to be understood that the invention is not limited to the specific embodiments thereof except as defined in the appended claims.

CLAIM OF PRIORITY

This application claims priority from Japanese Patent Application No. 2004-368686 filed on Dec. 21, 2004, which is hereby incorporated by reference herein.

What is claimed is:

1. An ophthalmic apparatus comprising:
a detection unit which detects a vision fixation state of an eye to be examined;
a projection unit which projects a fixation mark onto a fundus of the eye; and
a fixation mark control unit which controls said projection unit,
wherein said projection unit includes a changing unit which changes a fixation mark to be projected onto the fundus, and said fixation mark control unit controls said changing unit to change a fixation mark to be projected onto the fundus when a vision fixation state detected by said detection unit does not satisfy a predetermined criterion,
wherein said projection unit includes a plurality of fixation mark forming units which form different fixation marks, and said changing unit changes a fixation mark to be projected onto the fundus by selecting a fixation mark forming unit, of said plurality of fixation mark forming units, which should be operated.

2. The apparatus according to claim 1, wherein said projection unit includes a fixation mark forming unit which forms a fixation mark, and said changing unit changes a fixation mark to be projected onto the fundus by causing said fixation mark forming unit to intermittently form a fixation mark.

3. The apparatus according to claim 1, wherein said projection unit includes a display device which forms a fixation mark, and said changing unit changes a fixation mark to be projected onto the fundus by changing a fixation mark formed by said display device.

4. The apparatus according to claim 1, wherein said detection unit includes:
an observation unit which observes an anterior ocular segment of the eye;
an alignment index detection unit which detects an index image reflected by a cornea of the eye upon projecting an alignment index onto the cornea; and
a line-of sight detection unit which detects a line of sight of the eye based on outputs from said observation unit and said alignment index detection unit.

5. The apparatus according to claim 4, wherein said line-of sight detection unit detects the line of sight of the eye by detecting a relative position between a pupil center position obtained based on an output from said observation unit and a position of an index image reflected by the cornea which is obtained based on an output from said alignment index detection unit.

6. The apparatus according to claim 4, further comprising:
a driving unit which aligns an optometric unit
including said detection unit and said projection unit; and
a driving control unit which operates said driving unit to set the eye and said optometric unit in a predetermined positional relationship on the basis of an output from said alignment index detection unit.

7. The apparatus according to claim 1, further comprising an examination unit which examines information unique to the eye in a state in which a vision fixation state detected by said detection unit satisfies the predetermined criterion.

8. The apparatus according to claim 7, further comprising an output unit which displays or prints an output from said examination unit and an output from said detection unit.

9. An ophthalmic apparatus comprising:
an observation unit which observes an anterior ocular segment of an eye to be examined by illuminating the anterior ocular segment and sensing an image thereof;
an alignment index detection unit which detects a cornea reflected index image of an alignment index for position detection upon projecting the alignment index onto the cornea of the eye;
a line-of sight detection unit which detects a line of sight of the eye based on outputs from said observation unit and said alignment index detection unit;
a determination unit which determines whether a vision fixation state of the eye detected by said line-of-sight detection unit satisfies a predetermined condition;
a fixation mark projection unit which projects a fixation mark onto a fundus of the eye;
a fixation mark presentation changing unit which changes a presentation method for the fixation mark projected by said fixation mark projection unit; and
an arithmetic processing unit,
wherein when said determination unit determines that a vision fixation state detected by said line-of sight detection unit does not satisfy the predetermined condition, said arithmetic processing unit controls said fixation mark presentation changing unit to change the presentation method for the fixation mark.

10. The apparatus according to claim 9, wherein said line-of sight detection unit includes a pupil center detection unit which detects a pupil center position of the eye from an output from said observation unit, and detects the line of sight of the eye by detecting a relative position between an index image position detected by said alignment index detection unit and the pupil center position.

11. The apparatus according to claim 9, further comprising:
a driving unit which drives an optometric unit including at least said observation unit, said alignment index detection unit, and said fixation mark projection unit in three axis directions with respect to the eye;
an misalignment detection unit which detects an amount of misalignment between said optometric unit and a predetermined position on the eye on the basis of an output from said alignment index detection unit; and
a driving unit controller which controls said driving unit based on an output from said misalignment detection unit so as to set said optometric unit and the eye in a predetermined positional relationship,
wherein a vision fixation state of the eye is detected by subtracting an output from said misalignment detection unit from an output from said line-of sight detection unit.

12. The apparatus according to claim 9, further comprising:
an eye examination unit which examines information unique to the eye; and
an output unit which displays or prints information representing a vision fixation state detected by said line-of sight detection unit upon adding the information to an examination result obtained by said eye examination unit.

13. The apparatus according to claim 9, wherein
said fixation mark projection unit or said fixation mark presentation changing unit includes a light source for fixation mark illumination which illuminates the fixation mark and a fixation mark illumination light source driving unit which controls said light source for fixation mark illumination, and
said arithmetic processing unit controls said fixation mark illumination light source driving unit to change a lighting state of said light source for fixation mark illumination, thereby changing the presentation method for the fixation mark.

14. The apparatus according to claim 9, wherein
said fixation mark projection unit or said fixation mark presentation changing unit includes:
a plurality of fixation marks which are arranged at optically conjugate positions and have different shapes;
a plurality of light sources for fixation mark illumination which illuminate said plurality of fixation marks, respectively; and
a fixation mark illumination light source driving unit which controls said plurality of light sources for fixation mark illumination, and
said arithmetic processing unit controls said fixation mark illumination light source driving unit to change lighting states of said plurality of light sources for fixation mark illumination, thereby changing the presentation method for the fixation mark.

15. The apparatus according to claim 9, wherein
the fixation mark is formed by a liquid crystal panel and a backlight,
said fixation mark presentation changing unit is configured to change a shape or size of a fixation mark to be presented to the eye by controlling the liquid crystal panel, and
said arithmetic processing unit controls said fixation mark presentation changing unit to change the shape or size of the fixation mark, thereby changing the presentation method for the fixation mark.

16. The apparatus according to claim 10, wherein said line-of sight detection unit detects a line of sight when a cornea reflected index image is detected by said alignment index detection unit and a pupil center is detected by said pupil center detection unit.

17. The apparatus according to claim 9, further comprising an eye examination unit which examines information unique to the eye,
wherein said arithmetic processing unit executes detection of a line of sight of the eye by said line-of sight detection unit and determination of a vision fixation state of the eye by said determination unit in association with examination by said eye examination unit.

18. The apparatus according to claim 9, wherein said determination unit determines whether a variation in relative position between the pupil position and the alignment index image position satisfies the predetermined condition, depending on whether the variation falls within a predetermined range within a predetermined period of time.

19. An ophthalmic apparatus comprising:
an image sensor configured to sense an anterior ocular segment of an eye to be examined;
a detector configured to detect an index image reflected by a cornea of the eye;
a determination unit configured to determine a vision fixation state of the eye based on a change in a relative position of a pupil of the eye sensed by said image sensor and a position of the index image detected by said detector; and
a projection unit configured to project a fixation mark to the eye, wherein said projection unit is configured to change a fixation mark to be projected to the eye based on the vision fixation state determined by said determination unit.

20. An ophthalmic apparatus comprising:
an image sensor configured to sense an anterior ocular segment of an eye to be examined;
a detector configured to detect an index image reflected by a cornea of the eye;
a determination unit configured to determine a vision fixation state of the eye based on a change in a relative position between a position of a pupil of the eye sensed by said image sensor and a position of the index image detected by said detector; and
a projection unit configured to project a fixation mark to the eye, wherein said projection unit is configured to change a fixation mark to be projected to the eye based on the vision fixation state determined by said determination unit.

* * * * *